(12) United States Patent
Slade

(10) Patent No.: US 6,215,304 B1
(45) Date of Patent: Apr. 10, 2001

(54) NMR SENSOR

(75) Inventor: Robert Andrew Slade, Witney (GB)

(73) Assignee: Oxford Instruments (UK) Ltd., Oxon (GB)

( * ) Notice: Subject to any disclaimer, the term of this patent is extended or adjusted under 35 U.S.C. 154(b) by 0 days.

(21) Appl. No.: 09/232,697

(22) Filed: Jan. 19, 1999

(30) Foreign Application Priority Data

Jan. 21, 1998 (EP) .................................................. 98300433
Jan. 21, 1998 (EP) .................................................. 98300437

(51) Int. Cl.[7] .................................................. G01V 3/00
(52) U.S. Cl. ............................................ 324/303; 324/318
(58) Field of Search .................................. 324/303, 318, 324/319, 322

(56) References Cited

U.S. PATENT DOCUMENTS

| 4,629,986 | 12/1986 | Clow et al. ............................ 324/303 |
| 4,644,313 | 2/1987 | Miyajima .............................. 335/296 |
| 5,610,522 | 3/1997 | Locatelli et al. ..................... 324/319 |

FOREIGN PATENT DOCUMENTS

| 237 323 | 9/1987 | (EP) . |
| 581 666 | 2/1994 | (EP) . |
| 0 646 806 | 4/1995 | (EP) . |
| 0 691 548 | 1/1996 | (EP) . |
| 2 310 935 | 9/1997 | (GB) . |
| WO 99 36801 | 7/1999 | (WO) . |

OTHER PUBLICATIONS

Patent Abstracts of Japan, Abstract of JP 03205029 (Jun. 9, 1991).

H. Štěpánkovlá et al, "Fe NMR Study of Magnetization Processes in Barium Hexaferrites", Journal of Magnetism and Magnetic Materials, 157/158, 1996, pp. 393–394.

Primary Examiner—Jay Patidar
Assistant Examiner—Brij B. Shrivastav

(57) ABSTRACT

An NMR sensor including a magnetic field generating assembly, an RF antenna, and a plurality of ferrite members which couple with RF magnetic fields transmitted or received by the RF antenna. The sensor is typically used in apparatus for performing borehole measurements.

14 Claims, 8 Drawing Sheets

NMR SENSOR

BACKGROUND AND SUMMARY OF THE INVENTION

The present invention relates to an NMR sensor.

A measurement-while-drilling tool is described in EP-A-0581666 (Kleinberg) The tool comprises a tubular drill collar; a drill head positioned at an axial end of the drill collar; and an NMR sensor. The NMR sensor comprises a pair of tubular main magnets (which generate a static ($B_0$) magnetic field) each located in an internal recess of the drill collar, and an RF antenna located in an external recess in the drill collar between the main magnets. The RF antenna recess is optionally filled with a magnetically soft ferrite to improve the efficiency of the antenna.

An NMR well logging system is described in U.S. Pat. No. 4629986 (Clow et al.). A pair of main magnets are separated by a gap in which a solenoid RF antenna is symmetrically disposed. The solenoid has a core of high permeability ferrimagnetic material (soft ferrite).

A problem with the prior art systems is that dimensional resonances can be induced in the ferrite by the RF electromagnetic field. This absorbs energy and reduces RF efficiency.

In accordance with the present invention there is provided an NMR sensor comprising a magnetic field generating assembly; an RF antenna; and a plurality of ferrite members which couple with RF magnetic fields transmitted or received by the RF antenna.

The ferrite members boost the Q of the RF antenna and compensate for the effects of eddy currents. Typically the ferrite members are soft ferrite members.

By splitting the ferrite into a plurality of separate members, dimensional resonance in the ferrite is minimised. In particular, this enables the ferrite members to each have a maximum dimension less than half the wavelength of the lowest order standing wave which could otherwise be set up in the ferrite.

The ferrite members may be separated by air gaps or by a suitable filler such as epoxy resin. The ferrite members may each comprise a separate particle in a single epoxy resin matrix. In a limiting case the ferrite members may be physically in contact. However at a microscopic level the members will only be in contact at points, and standing waves will still be substantially attenuated by the crystal discontinuities between the members.

Apart from minimising dimensional resonances, the provision of plural ferrite members provides an additional degree of freedom in the geometrical arrangement of the ferrite. Therefore the relative sizes and positions of the ferrite members can be selected to optimise the $B_0$ and RF field profiles. The effect of ferrite on the $B_0$ and RF field profiles has not previously been fully recognised in the prior art. It is important that the B field shape is optimised to maximise radial shell thickness to reduce susceptibility to lateral tool motions (such as vibration and whirl) whilst maintaining sufficient signal-to-noise ratio. In particular, unless care is taken in the design, the static magnetic field will tend to saturate the soft ferrite, reducing its relative permeability to unity and negating any improvements in RF efficiency. Similarly, the soft ferrite will modify the $B_0$ field profile, thereby changing the shape and position of the sensitive volume from which NMR signal arises. Both of these related effects must be considered in the design of a real sensor.

Various BO field profiles are achievable by adjusting the size and axial position of the soft ferrite members: it is possible to cancel the first and second order radial gradients to create a "radially optimised" field profile, as described by Hanley in U.S. Pat. No. 5471140, or alternatively to cancel the first order axial field gradient to generate an "axially optimised" field profile, as described in EP-A-0774671, or to shim the field for uniform BO magnitude for an "intermediate" field profile, as described by Slade in PCT/GB98/02398. Unlike this prior art, the BO field manipulation is achieved using the placement of soft ferrites only; no hard ferrite permanent magnet shims need be employed.

Furthermore, in a similar fashion adjustment of the soft ferrite members can be used to reposition the small crescent-shaped resonant regions, known as "borehole lobes" and shown in FIG. 6, which can produce unwanted NMR signal from the borehole region. The lobes can be moved until they are partially or wholly within the outside diameter of the tool. In this way they cannot generate a significant borehole NMR signal.

Typically the NMR sensor is an "inside-out" sensor which performs measurements on an external sample outside the space envelope of the magnetic field generating assembly and the RF antenna.

The sensor may be employed in a variety of applications. However typically the sensor is provided in apparatus for performing borehole measurements in a formation.

The apparatus may be a wireline tool which performs measurements after the borehole has been drilled. However in a preferred example the apparatus is a measurement-while-drilling (MWD) tool which is provided with a drill head at an axial end of a support whereby the apparatus can carry out NMR measurements during drilling of the borehole. The tool may be a logging-while-drilling (LWD) or formation-evaluation-while-drilling (FEWD) tool in which the NMR information relating to the formation is stored on in-board memory for retrieval when the tool is returned to the surface. Alternatively a telemetry system may be provided and the NMR information is used to control the drill in real time (i.e. steering).

The ferrite has the unavoidable effect of reducing the inner diameter of the working volume in comparison with similar sized logging tools using permanent magnet shims as described by Hanley in U.S. Pat. No. 5471140 and EP-A-0774671. This results in a loss of penetration depth. However this is less of a disadvantage in a MWD tool because the invasion of the formation by borehole fluids occurs slowly after drilling. The MWD tool generally arrives at the formation less than an hour after cutting, whereas a wireline tool can arrive days or weeks later. As a result there will be less borehole fluid in the formation under study and so the use of ferrite is particularly suited to a MWD tool.

Furthermore a typical MWD tool has a larger radius than a comparable wireline tool. Since the $B_0$. strength scales approximately as the second power of the magnet mean radius, it is possible to space the main magnets farther apart in an MWD tool using larger diameter main magnets and thus regain some of the penetration depth.

The ferrite members may be axially spaced and/or spaced at right angles to the axis of the tool. A primary consideration in the design of an NMR MWD tool is making the NMR measurement insensitive to the effect of lateral tool motions, such as vibration and whirl. To a first approximation it is clear that it will not be possible to re-focus the NMR signal in the sensitive region if the tool is displaced laterally (i.e. in a direction parallel to the radius) during the pulse sequence by a distance which is a significant proportion of the radial thickness of the sensitive shell. It is therefore necessary to select a $B_0$ optimisation scheme and RF bandwidth such that the shell thickness is much larger than the maximum expected lateral displacement. Little is known about the precise motions of drilling tools down hole, but the typical range of displacement is from 1 to 10 mm at frequencies of a few Hz.

Rotation periods are between 1 and 3Hz. The typical NMR mea0surement lasts from 50 ms to 1s, so these motions are significant. However, the flexible nature of the sensor according to the present invention ensures that it is possible to design a tool with a sensitive shell thicker than the maximum expected motion. The tool described in the preferred embodiment has a shell with a radial thickness about 20 mm and axial length about 50 mm.

In comparison to a wireline borehole logging tool, an MWD tool has to be significantly stronger to support the drilling forces. In particular, as the sensor forms part of the drill collar, it has to be able to withstand the torsional and bending loads imposed by the rotating drilling action. It is therefore preferred that the entire sensor support structure is metal, such as stainless steel or titanium. However, the RF antenna will introduce localised parasitic eddy currents in the metallic structure of the tool which can seriously impair RF efficiency. It is therefore necessary to consider how to minimise the impact of the all-metal structure on the RF field.

The arrangement that gives the best mechanical strength and RF efficiency is achieved by winding the RF antenna as a solenoid in an external recess as described in EP-A-0581666. The skin depth in stainless steel at the typical operating frequency of 0.5 MHz is less than a few millimetres. Eddy currents will therefore flow in the surface of the drill collar under the RF coil, mirroring the driving current and effectively restricting the RF flux to the radial gap between the reduced drill collar outer diameter and the RF coil inner diameter. The RF coil diameter is made as large as possible consistent with the tool diameter, but it is desirable to make the coil recess as shallow as possible to minimise the loss in mechanical strength in this region. However, as the recess is made radially shallower, the gap decreases and the inductance of the RF transmit coil decreases, hence the RF field strength in the sensitive region for a fixed coil current decreases, hence requiring longer pulses, thus resulting in narrower bandwidth, reduced sensitive volume and lower signal strength. If the coil current is increased to compensate, the power requirement rises as the second power of current, so this too is undesirable. In practice the recess is made as deep as possible, consistent with adequate tool strength, and the loss in RF efficiency due to eddy currents is compensated by inserting soft ferrite into the gap between the RF coils and the recess base.

This places constraints on the design of the NMR sensor and can result in reduced mechanical strength. Therefore in a preferred embodiment the apparatus further comprises a recess formed in the support, the recess having a base and a pair of axially spaced shoulders, wherein the ferrite members are located at least partially in the recess; and one or more strengthening members which are arranged between the ferrite members, coupled to the base of the recess, and coupled to each shoulder of the recess. The strengthening member(s) increase the torsional and bending strength of the tool. As a result the depth of the recess can be greater than in the prior art without decreasing the strength of the tool.

Electromagnetic finite element analysis shows that the eddy currents flow around the strengthening member(s) and the perturbation to the RF field in the sensitive volume is minimal.

Typically the RF antenna comprises a coil which is wound over the ferrite members.

Typically the magnetic field generating assembly comprises a pair of axially spaced main magnets having opposite pole orientation (i.e. like poles facing each other), and the RF antenna is located axially between the pair of main magnets. This provides a rotationally invariant radial static magnetic field which is particularly important in a MWD tool.

Additional RF power losses will occur if a dimension of the ferrite is large enough to support a standing wave between the boundaries made by the external faces of the ferrite. The lowest mode is a half wavelength. The wavelength $\lambda$ is related to the RF frequency (f) and the speed of propagation of EM waves in the ferrite (v), which is in turn related to the ferrite's relative permeability ($\mu$) and permittivity ($\epsilon$):

$$\lambda = \frac{v}{f} \qquad v = \frac{c}{\sqrt{\mu \cdot \epsilon}}$$

where c is the speed of light in vacuum. Selection of soft ferrite material with the correct combination of permeability and permittivity is therefore necessary.

Soft ferrites are all based on iron oxide compounds, but their properties are influenced by the other metallic ions in their structure. Soft ferrite used at less than 200 MHz are typically of cubic spinel crystalline structure, with chemical composition $M^{2+}Fe_2^{3+}O_4$, where $M^{2+}$ represents a metallic ion and is either $Ni^{2+}$, $Mn^{2+}$, $Mg^{2+}$, $Zn^{2+}$, $Cu^{2+}$, $Co^{2+}$, or mixtures of these, most commonly MnZn and NiZn. These are commonly referred to as Maganese-Zinc ferrite and Nickel-Zinc ferrite. The NiZn ferrites have typically 10000 times higher resistivity than the MnZn ferrites, so are better suited to operation above 100 kHz, due to their reduced eddy current loss. However, in addition, MnZn ferrites have electrical permittivity typically $10^5$, compared to about 100 for NiZn. Assuming a typical relative permeability of about 5000 for both types, the EM wave propagation velocity is therefore $1.3 \times 10^4$ m/s in MnZn ferrite and $4 \times 10^5$ m/s in NiZn ferrite. So at an operating frequency of about 0.5 MHz, a half wavelength is only 13 mm in MnZn ferrite and 210 mm in NiZn. To avoid power losses due to dimensional resonances it is therefore preferred that the largest dimensions of any one piece of ferrite are less than these values. So NiZn ferrites are preferred because MnZn pieces would need to be very small and hard to make.

The choice of soft ferrite material is further complicated by the property of magnetostriction exhibited by all ferrite. This phenomenon is a microscopic change in the physical dimensions of the ferrite under the influence of magnetic field. After the application of an RF pulse, the ferrite structure "rings" like a bell as stored energy dissipates. In a practical design it is necessary to minimise the amount and duration of ringing as too much ringing can disable the NMR receiver. The most accurate NMR measurements are made when RF pulses in a CPMG sequence are applied as rapidly as possible. As the NMR echo is acquired at a point in time midway between RF pulses, it is necessary to minimise the system "deadtime"—the time taken for the receiver system to recover from an RF pulse. A high degree of magnetostriction will increase the deadtime, so it is desirable that the ferrite used has a low coefficient of magnetostriction. Unfortunately, NiZn ferrite has a coefficient of magnetostriction 3 to 5 times greater than MnZn ferrite. Therefore, if MnZn ferrite is used, the individual pieces must be small enough such that dimensional resonances are not excited—less than about 13 mm in all dimensions in the example given. Many more pieces will be required, but this can even be an advantage from a manufacturing standpoint.

To avoid resonances in the MnZn ferrite shims it is preferred to keep all their dimensions below about 13 cm. Therefore in a preferred embodiment the ferrite members are split into at least thirty seven (in this example) arc segments (as the circumference of the soft ferrite ring shims described in the 6.75" outer diameter preferred embodiment tool is 48 cm), and splitting them axially into separate axially spaced rings (at a spacing of less than 13 mm) each comprising a plurality of separate arc segments.

BRIEF DESCRIPTION OF THE DRAWINGS

Some embodiments of the present invention will now be described with reference to the accompanying drawings, in which.

DETAILED DESCRIPTION OF THE PREFERRED EMBODIMENTS

Figure 1:
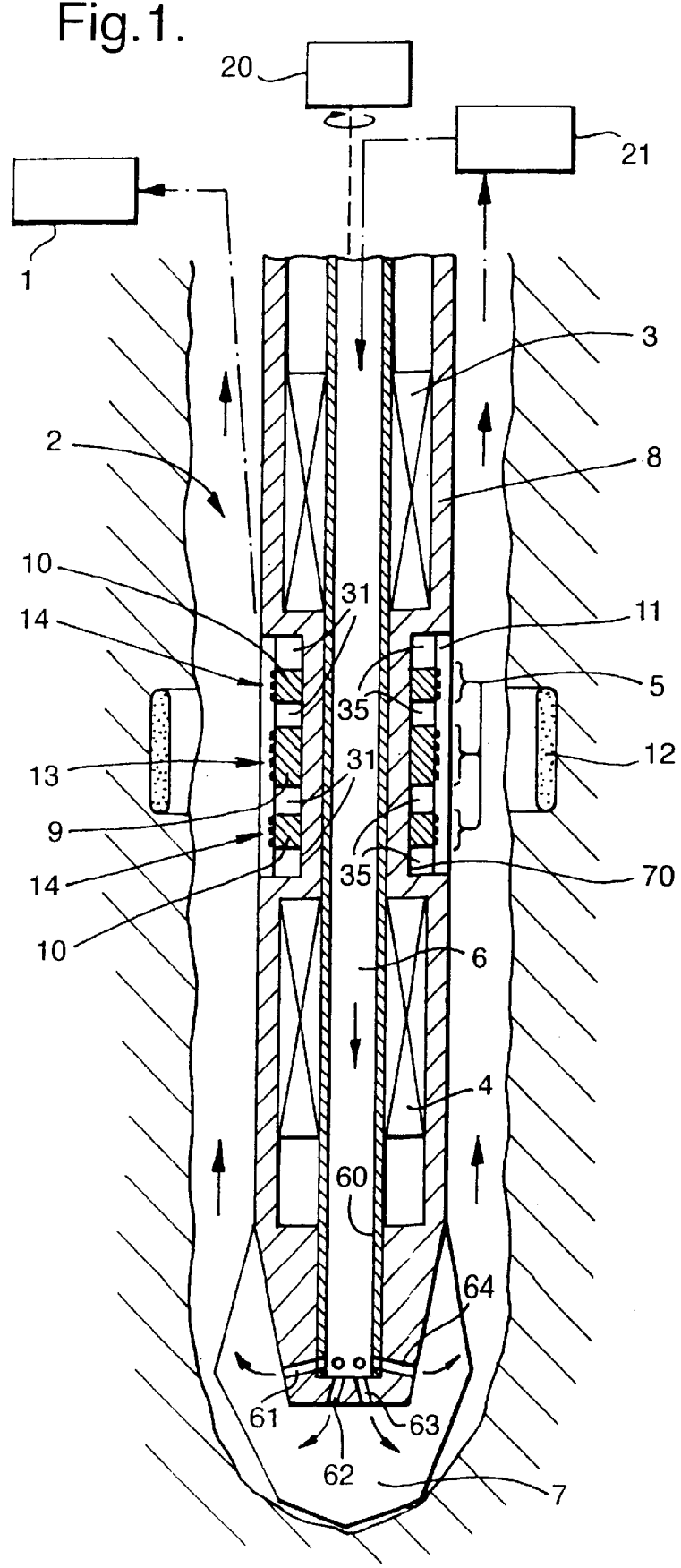
FIG. 1 is a schematic cross-section of a NMR measurement-while-drilling tool drilling a borehole.

Referring to FIG. 1, the tool has a drill head 7 at one end, a sensor section 2 behind the drill head, and electronics 1.

The sensor section 2 comprises a magnetic field generating assembly for generating a $B_0$ magnetic field (which is substantially time invariant over the duration of a measurement), and an RF system for transmitting and receiving RF magnetic pulses and echoes. The magnetic field generating assembly comprises a pair of axially spaced main magnets 3,4 having opposite pole orientations (ie. with like magnetic poles facing each other), and three ferrite members 9,10 axially arranged between the main magnets 3,4. The ferrite members are made of "soft" ferrite which can be distinguished over "hard" ferrite by the shape of the BH curve which affects both intrinsic coercivity ($H_{cj}$, the intersection with the H axis) and initial permeability ($\mu_i$, the gradient in the unmagnetised case). Soft ferrite $\mu_i$ values typically range from 100 to 10000 whereas hard ferrite $\mu_i$ is about 1. Therefore the soft ferrite has large initial permeability (typically greater than 100, preferably greater than 1000). The RF system comprises a set of RF transmit antenna and RF receive antenna coil windings arranged as a central "field forming" solenoid group 13 and a pair of outer "coupling control" solenoid groups 14.

The tool has a mud pipe 60 with a clear central bore 6 and a number of exit apertures 61–64 to carry drilling mud to the bit 7, and the main body of the tool is provided by a drill collar 8. Drilling mud is pumped down the mud pipe 6 by a pump 21 returning around the tool and the entire tool is rotated by a drive 20.

Gaps in the pockets between the soft ferrite members are filled with non-conducting material which is not shown in FIG. 1 (eg: ceramic or high temperature plastic) and the RF coils 13,14 are then wound over the soft ferrite members 9,10. The soft ferrites 9,10 and RF coil assembly 13,14 are pressure impregnated with suitable high temperature, low viscosity epoxy resin (not shown) to harden the system against the effects of vibration, seal against drilling fluid at well pressure, and reduce the possibility of magnetoacoustic oscillations. The RF coils 13,14 are then covered with wear plates 11 typically ceramic or other durable non-conducting material to protect them from the rock chippings flowing upwards past the tool in the borehole mud.

Figure 2:
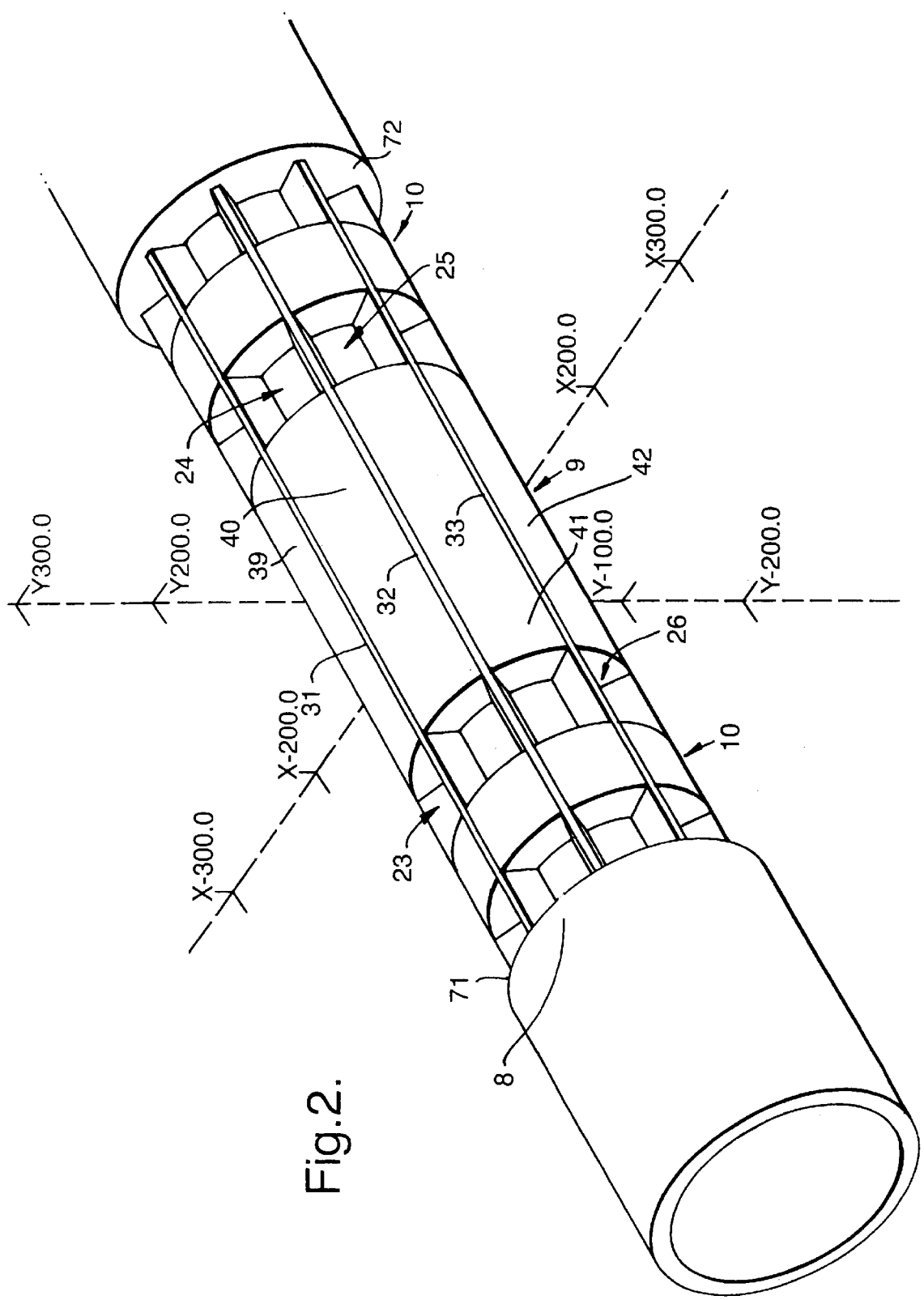
FIG. 2 is perspective view of part of the tool, with some parts removed.
Figure 3:
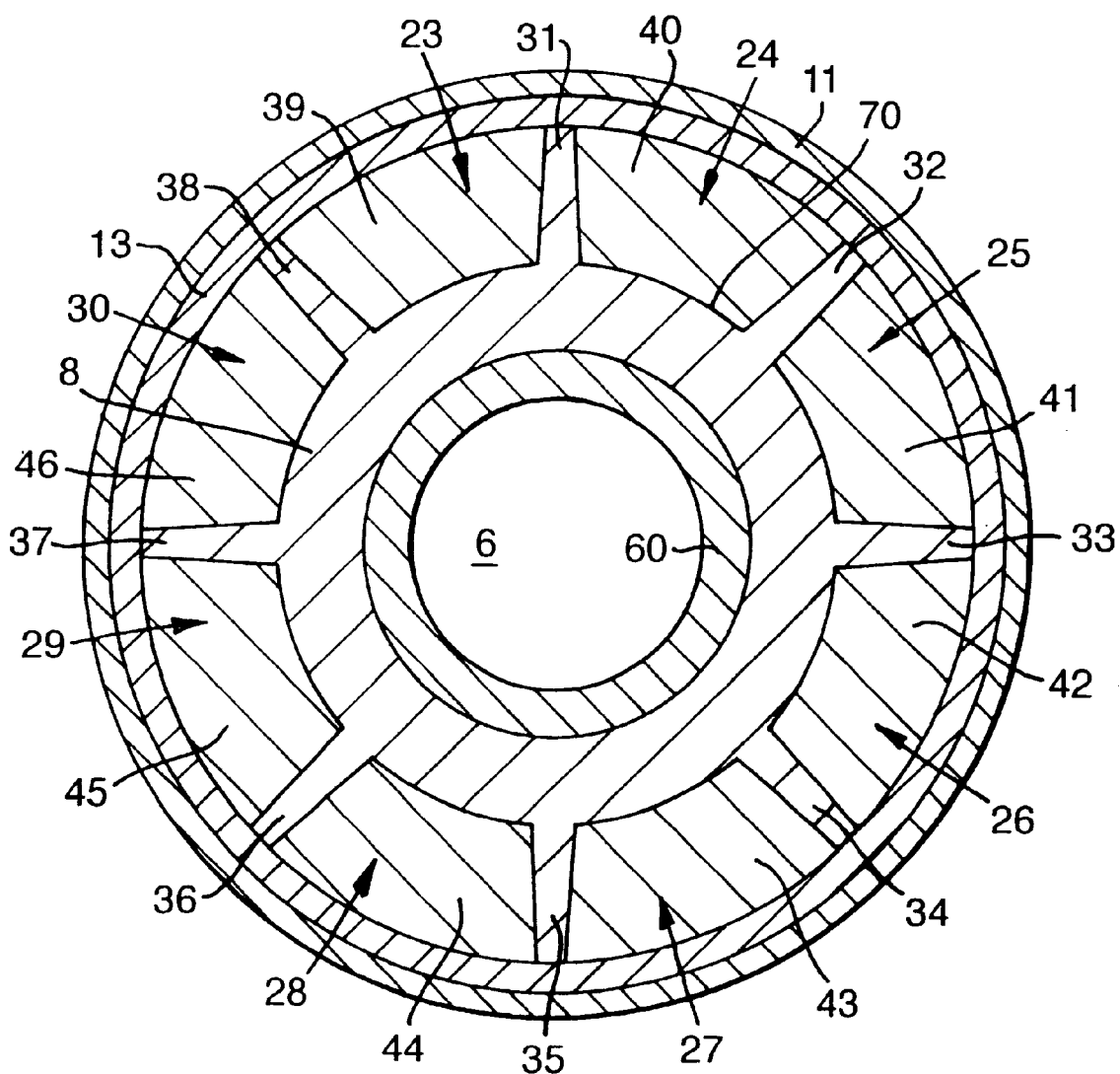
FIG. 3 is a cross-section through the centre plane of the tool.

The torsional and bending strength of the tool is improved by axial ribs or webs under the RF coils as shown in FIGS. 2 and 3.

FIG. 2 is a perspective view of part of the tool with the ceramic wear plates 11, RF coils 13,14 and non-conducting material 22 removed. The strengthening webs 31–38 and ferrite members 9,10 are clearly shown.

The drill collar 8 is constructed by machining a stainless steel cylinder with a bore to receive the mud pipe 6, enlarging the inside diameter for the cylindrical main magnet poles 3,4 and milling eight axial pockets 23–30 in the outer radial periphery of the collar 8 separated by eight axial ribs (or webs) 31–38. This results in an annular recess in the outer periphery of the collar with a base 70 (shown in FIG. 1) and eight axial ribs 31–38 which project from the base 70 and extend between the two axial shoulders 71,72 of the recess. The soft ferrite members 9,10 are built up from arc segments mounted in the axial pockets 23–30. For instance the central member 9 is formed from eight arc segments 39–46. The axially oriented ribs 31–38 stiffen the reduced diameter section of drill collar under the RF coils. Surprisingly, the effect of the ribs 31–38 on the RF field profiles has been found to be quite negligible in the sensitive region by using commercial 3D FEA software to re-analyze the RF fields in the presence of the ribs 31–38.

Figure 4:
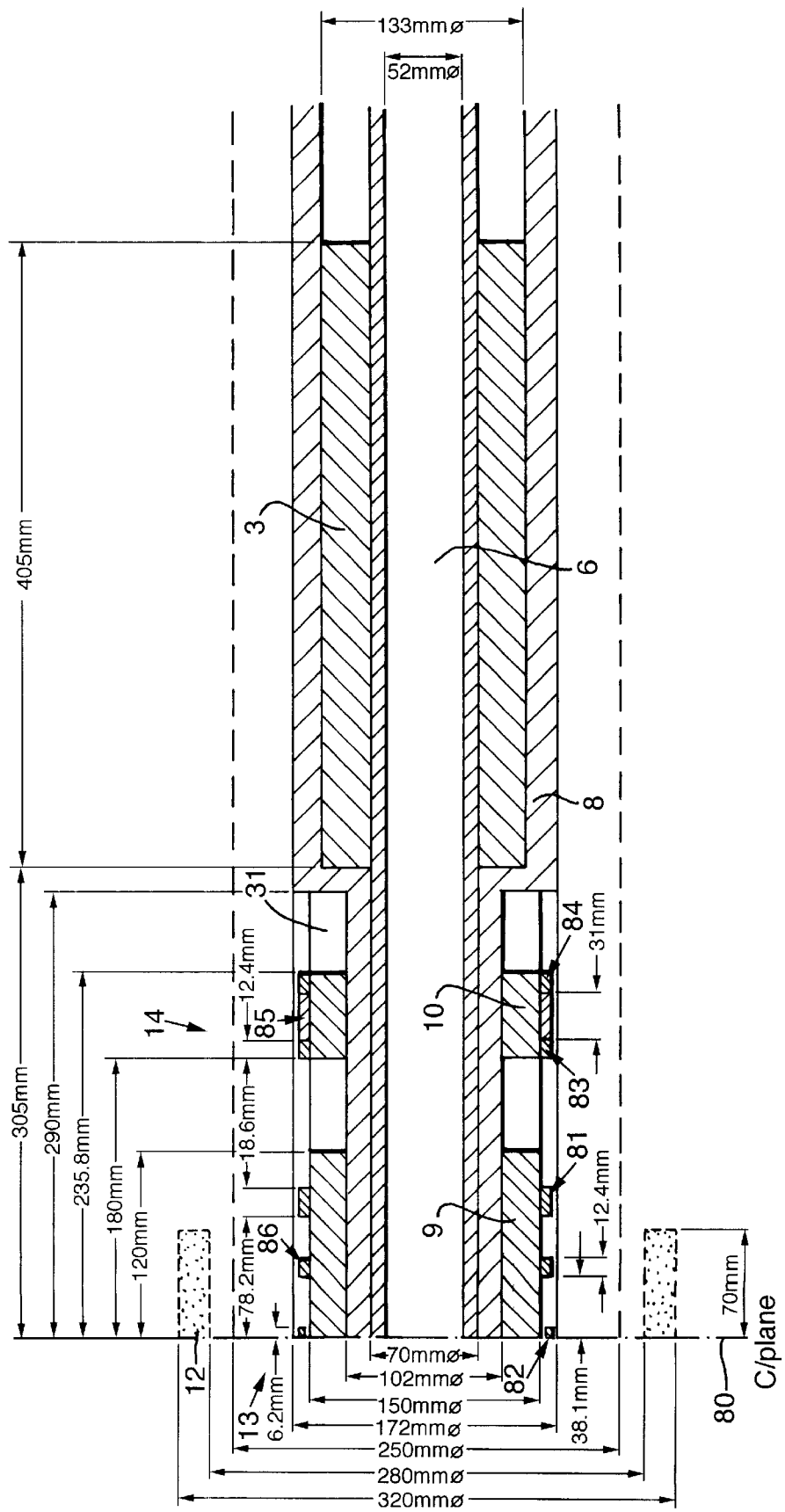
FIG. 4 illustrates the dimensions of the tool.

The precise dimensions of the sensor are shown in FIG. 4. The sensor is symmetrical about centre plane 80. FIG. 4 also shows the RF solenoid groups 13,14 in detail.

The central "field forming" solenoid group 13 comprises three positively wound transmit coil winding groups and two receive coil winding groups all wound in the same sense. Each winding group comprises a number of solenoidal turns. FIG. 4 shows one of the two outer transmit coil winding groups 81 (the other being located on the opposite side of centre plane 80), half of the central transmit coil winding group 82 (the other half being located on the opposite side of centre plane 80), and one of the two receive coil winding groups 86 (the other being located on the opposite side of centre plane 80).

Each "coupling control" solenoid group 14 comprises a pair of receive coil winding groups 83,84 wound in the same sense as the field forming winding groups and a transmit coil winding group 85 wound in the opposite sense. All coils in both groups allocated to the transmit coil are series connected as are all those allocated to the receive coil. The coil and number of turns positions are selected to produce substantially uniform axially oriented RF flux across the sensitive volume, thus creating conditions for NMR, whilst simultaneously cancelling the mutual inductance of the transmit and receive coils. The system of "zero-coupling coils" is described in EP-A-0837338. Furthermore, as also described in EP-A-0837288, the design of the twin RF coil system is such that it does not generate any NMR signal within the borehole region (for example, from vestigial borehole lobes). Consequently, the present invention does not require the use of gradient coils to cancel borehole signal, as described in EP-A-0581666 (Kleinberg).

The $B_0$ magnetic field is shimmed to the desired profile by adjusting the length and position of the soft ferrite members 9,10. A soft ferrite material grade is chosen which combines the following properties: high saturation flux density ($B_{sat}$>250 mT, such that the static B0 field does not saturate the ferrite), high resistivity (>$10^5$ $\Omega$m, so that RF eddy current losses are negligible), high Curie temperature (>150° C., so that operation in a typical well environment is possible), low drift in properties with temperature, and minimum hysteresis (to minimise RF hysteresis losses), and minimum magnetostriction. There is a huge variation in the properties of commercially available soft ferrite, but many NiZn and MnZn ferrites have suitable properties.

Figure 5:
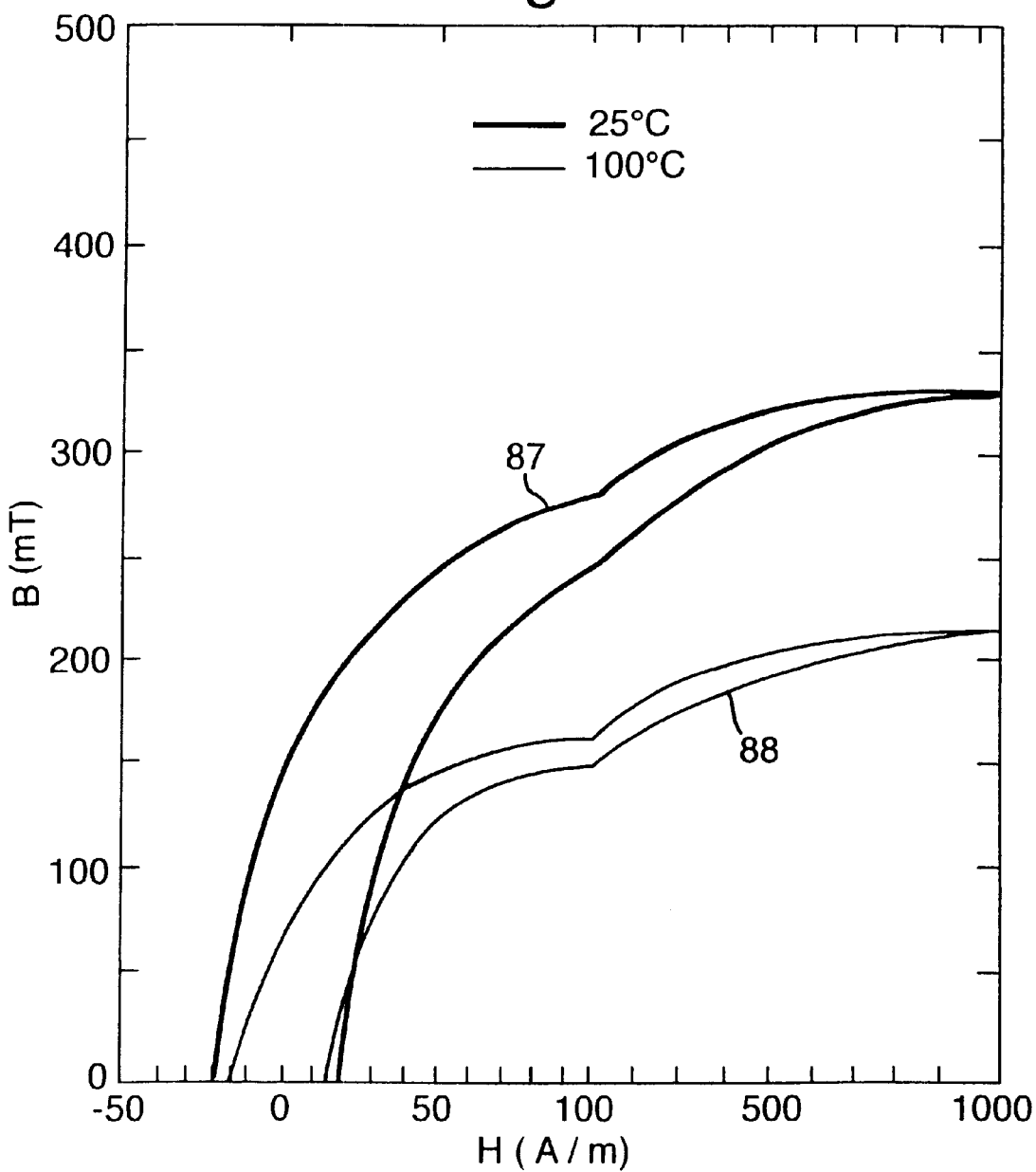
FIG. 5 shows BH curves of a suitable ferrite.

FIG. 5 shows two BH curves of a suitable grade of ferrite. The upper curve 87 is the curve at 25° C. and the lower curve 88 is the curve at 100° C.

Magnet pole material for the main magnets 3,4 is chosen for maximum remanence ($B_r$ ~1.1T, to generate the strongest possible field), high intrinsic coercivity ($H_{CJ}$ ~800 kA/m, to resist demagnetisation in the presence of external ferromagnetic structures, such as steel borehole cladding), high Curie temperature (to resist the high temperature well environment) and low drift in properties with temperature. The most suitable materials are Samarium Cobalt alloys ($Sm_2Co_{17}$), although Neobdinium Iron Boron materials have many advantages, but are more affected by temperature. The poles 3,4 are premagnetised along their axis.

As described above, the soft ferrite material is chosen with a high saturation flux density so that the static B0 field does not saturate the ferrite. The working point of the ferrite on the BH curve at each point within its volume therefore varies depending on the local magnetic field intensity due to the main magnet poles, but in all cases the working point is on the lower third to half of the initial linear gradient section. (The precise gradient and offset depend on the previous magnetic history and hysteresis characteristics of the ferrite). The slope of the BH curve is a measure of the relative permeability of the material, which is typically 200–6000 for soft ferrite grades suitable for the application. When alternating current is passed though the RF transmit coil at the resonant frequency during an RF pulse, the flux density within the ferrite is boosted by the permeability of the ferrite, and the ferrite is taken repeatedly around a minor hysteresis loop with each cycle of the RF. As long as the RF B1 field does not cause the ferrite to saturate, (ie: move out of the linear portion of the major BH curve) the RF flux density in the sensitive volume will be increased dramatically by the presence of the ferrite. Saturation is avoided by limiting the current density in the RF coils. Typically the increase in B1 flux density achieved, when compared with the same current in the same coil, without ferrite and without the stainless drill collar, will be a factor of 3–6, depending on coil geometry, and a factor of 6–12 over the flux density from the same current in the same coil, without the ferrite but with the drill collar. This is a very significant increase, resulting in a valuable saving in RF power. Some of this power can then be used to shorten the RF pulses, increase the system bandwidth and thereby increase the volume of the sensitive shell, hence increasing SNR and resistance to lateral motion effects.

The increased flux linking the RF coils as a result of the soft ferrite increases their inductance in a similar manner. It is therefore preferred that all the winding sections of both Tx and Rx coils are wound over ferrite and their inductances boosted in a similar way, so that the Tx-Rx mutual inductance of the "field forming" group is cancelled by the mutual inductance of the "coupling control" group, if zero coupling is to be achieved.

Figure 6:
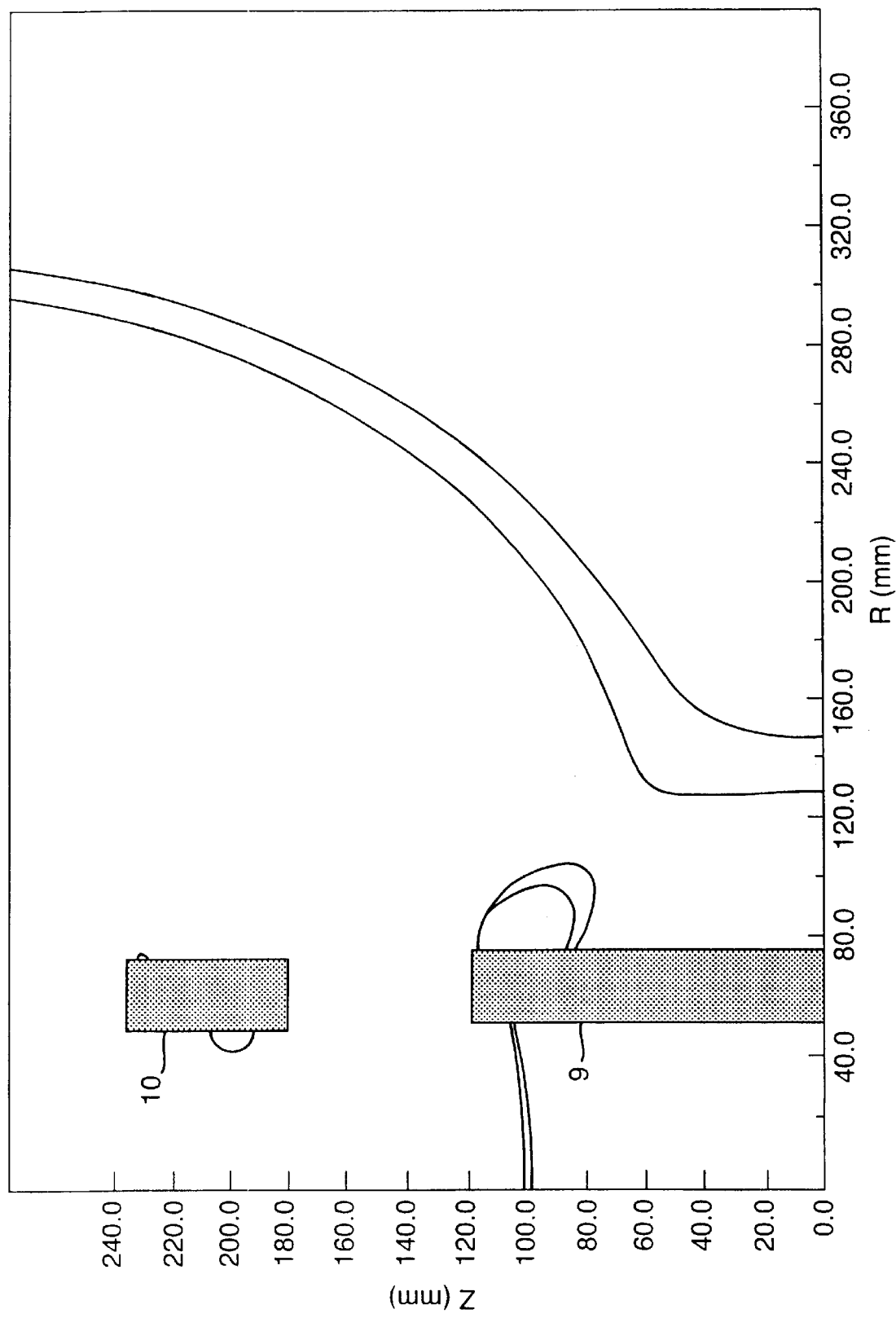
FIG. 6 is a contour plot of relative permeability $\mu$ over the ferrite members.

Analysis shows that for this embodiment it is not possible to position all of the RF coils over the single central soft ferrite member 9 and still maintain approximately uniform RF field profiles across the sensitive volume. It is possible to place the field forming group 13 over the central shim, but the coupling control group 14 needs to be positioned separately, for example, axially above the central shim. For zero coupling to be achieved between the Tx and Rx coils, it is therefore necessary to add the extra pair of soft ferrite disk members 10 under the coupling control RF coil groups 14. Obviously, these extra ferrite members 10 affect the B0 field profile significantly. However, by returning to the B0 analysis, it is possible to adjust the length of the centre shim 13 slightly to correct for the field distortion created by the new ferrite pair 10. Being closer to the main magnet poles 3,4 the additional ferrite pair 10 are in stronger magnetic fields and are closer to saturation than the central ferrite member 9. If the material grade is selected carefully, however, the ferrite pair 10 will remain on the linear part of the BH curve over the majority of their volume and retain a relative permeability comparable with the central shim. The relative permeability of the ferrite members 9,10 is shown in a contour plot in FIG. 6. In this way, it is possible to iteratively optimise the RF coil design and to meet the twin field profile and near zero-coupling design requirement. In a possible alternative embodiment, the coupling control coil groups, and their associated soft ferrite, can be physically removed entirely from the vicinity of the sensor, for example into the electronics module. The electrical connection and function of the various coils remains identical. In this embodiment, the magnet field shape can either be adjusted using only the central ferrite shim, or by adding other ferrite shims as required. These additional ferrite shims do not necessarily have RF coils wound over them.

Figure 7:
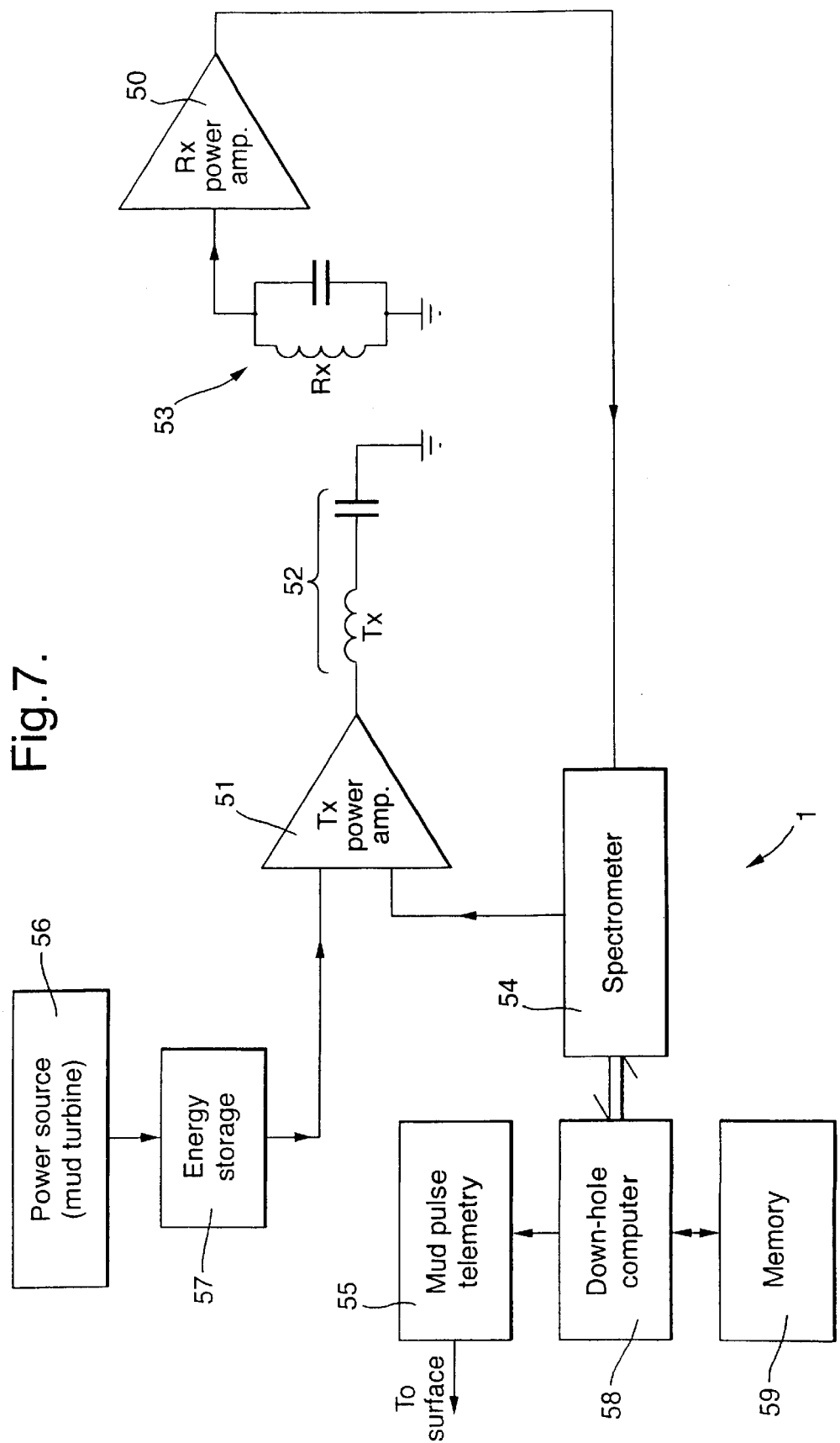
FIG. 7 illustrates the electronics system.

The electronics 1 illustrated in FIG. 7 is typically housed in a series of hermetically sealed pockets in the drill collar 8 above or below the sensor elements. Critical components, such as the receiver preamplifier 50, are located as close as possible to the tuned RF receive coil. The main components of the electronics required to interface with the NMR sensor are: a RF transmitter amplifier 51 to drive the transmit antenna 52, a low noise receiver pre-amplifier 50 connected to the receive antenna 53, a digital spectrometer 54 to schedule pulses and detect echoes, an associated down-hole computer 58 to analyze and compress the data and control the tool, electronic memory 59 for data storage and optionally a telemetry system 55 consistent with the drilling environment, such as a mud-pulse system. Power for the electronics is typically derived from a turbine generator 56 driven by the mud flow, and is quite limited, typically to 100W, so some form of on-board energy storage 57 is also required as the power dissipation during a pulse sequence will often exceed the input power.

Figure 8:
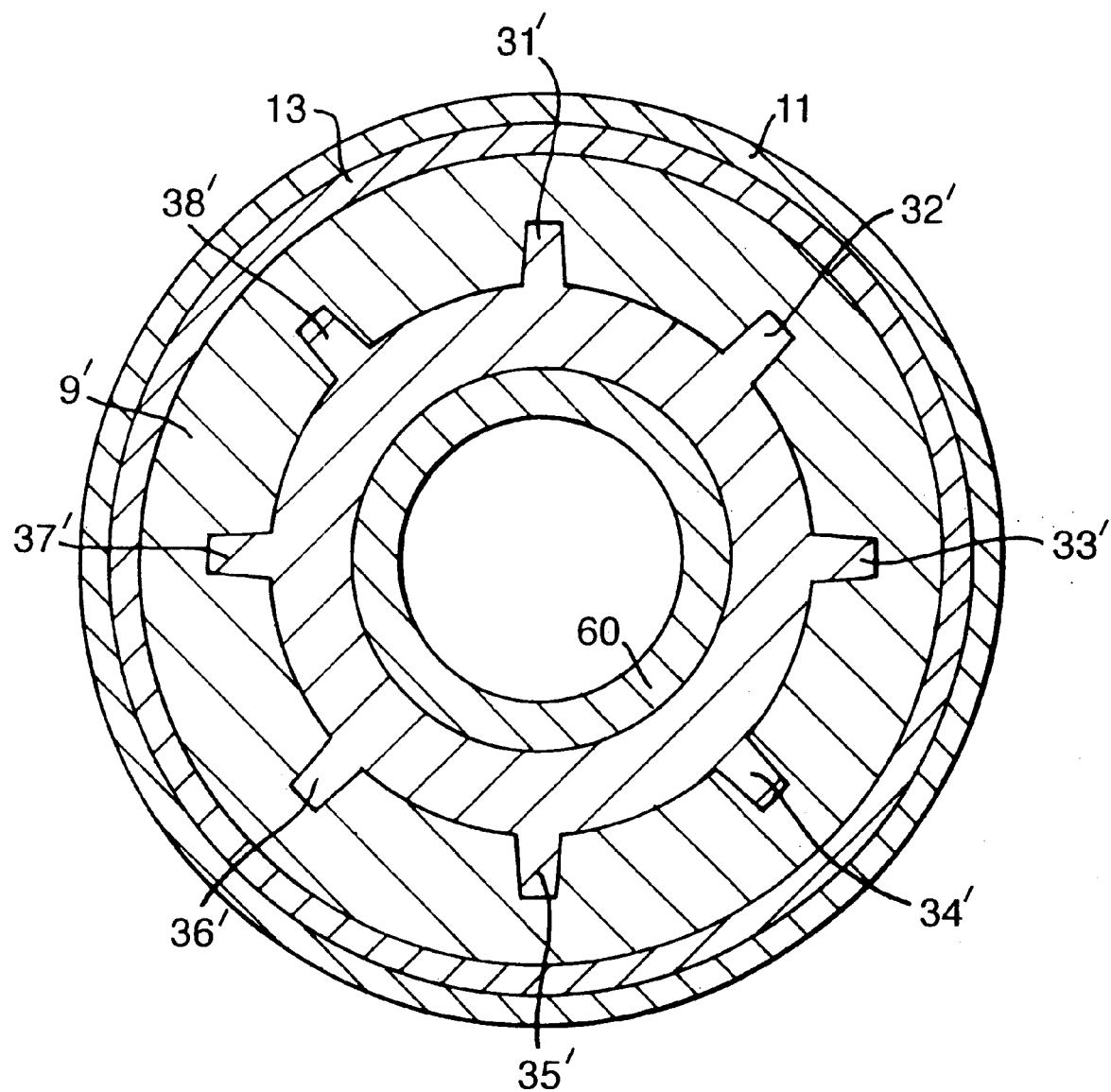
FIG. 8 is a view similar to FIG. 3 but of a second embodiment.

In a first alternative embodiment, the ferrite members 9,10 each comprise a unitary member having eight inner slots which receive strengthening ribs extending only partially between the inner and outer radial peripheries of the ferrite. The central ferrite member of such an alternative is shown in FIG. 8 (which corresponds with FIG. 3). The ribs 31'–38' extend half way into the unitary block of ferrite 9'.

In a second alternative embodiment (not shown) the central ferrite member 9 is split into a number of axially spaced sections, to reduce dimensional resonance.

In a third alternative embodiment (not shown), internal axial ribs similar to the ribs 31–38 are also formed in the recesses which house the main magnets 3,4, splitting the main magnets 3,4 into a number of segments. This allows the main magnet outer diameter to be increased resulting in a gain in $B_0$ field strength.

In a fourth alternative embodiment (not shown) the axial ribs 31–38 are omitted from the central RF antenna recess and strengthening ribs are only provided in the main magnet recesses.

In a fifth alternative embodiment (not shown), the axial ribs are omitted from both the RF antenna recess and the magnet recess.

I claim:

1. An NMR sensor, comprising:

a magnetic field generating assembly;

an RF antenna; and a plurality of ferrite members which couple with RF magnetic fields transmitted or received by the RF antenna.

2. A sensor according to claim 1, wherein a maximum dimension of each of the ferrite members is less than a half wavelength of electromagnetic waves within the ferrite material at the NMR operating frequency.

3. A sensor according to claim 1, wherein the RF antenna comprises a coil which is wound over the ferrite members.

4. A sensor according to claim 1, wherein the magnetic field generating assembly comprises a pair of axially spaced main magnets having opposite pole orientation, and the RF antenna is located axially between the pair of main magnets.

5. A sensor according to claim 1, wherein the sensor is arranged to perform measurements on an external sample outside a space envelope of the magnetic field generating apparatus and the RF antenna.

6. A sensor according to claim 1, wherein the magnetic field generating assembly has a radial gradient which is minimised with respect to variation in a size and a position of the ferrite members.

7. An apparatus for performing borehole measurements, comprising:

an NMR sensor including a magnetic field generating assembly;

an RF antenna; and a plurality of ferrite members which couple with RF magnetic fields transmitted or received by the RF antenna.

8. An apparatus according to claim 7, wherein the ferrite members are mounted on an elongate axially extending support, and the ferrite members are axially spaced.

9. An apparatus according to claim 7, wherein the ferrite members are mounted on an elongate axially extending support, and the ferrite members are arranged around an axis of the support at the same axial position.

10. An apparatus according to claim 8, further comprising:

a recess formed in the support, the recess having a base and a pair of axially spaced shoulders, wherein the ferrite members are located at least partially in the recess; and one or more strengthening members which are arranged between the ferrite members, coupled to the base of the recess, and coupled to each shoulder of the recess.

11. An apparatus according to claim 10, wherein the one or more strengthening members have a maximum dimension which is substantially parallel with an axis of the tool.

12. An apparatus according to claim 10, wherein the one or more strengthening members are fabricated from a material comprising a metal.

13. An apparatus according to claim 10, wherein the one or more strengthening members and the support comprise a unitary member.

14. An apparatus according to claim 7, further comprising a drill head mounted at an axial end of the support.

* * * * *